(12) United States Patent
Álvarez Ponce (10) Patent No.: US 11,065,145 B2
(45) Date of Patent: Jul. 20, 2021

(54) SPHINCTER-TYPE INTESTINAL VALVE

(71) Applicant: Carlos Eduardo Álvarez Ponce, Mexico City (MX)

(72) Inventor: Carlos Eduardo Álvarez Ponce, Mexico City (MX)

(*) Notice: Subject to any disclaimer, the term of this patent is extended or adjusted under 35 U.S.C. 154(b) by 389 days.

(21) Appl. No.: 16/063,013

(22) PCT Filed: Jan. 27, 2017

(86) PCT No.: PCT/IB2017/000045
§ 371 (c)(1),
(2) Date: Jun. 15, 2018

(87) PCT Pub. No.: WO2017/130055
PCT Pub. Date: Aug. 3, 2017

(65) Prior Publication Data
US 2018/0360644 A1 Dec. 20, 2018

(30) Foreign Application Priority Data

Jan. 29, 2016 (MX) .................. MX/a/2016/001395
Jan. 26, 2017 (MX) .................. MX/a/2017/001193

(51) Int. Cl.
*A61F 5/44* (2006.01)
*A61F 5/445* (2006.01)

(52) U.S. Cl.
CPC ............ *A61F 5/445* (2013.01); *A61F 5/4405* (2013.01); *A61F 2005/4455* (2013.01)

(58) Field of Classification Search
CPC ............ A61F 2005/4455; A61F 5/4405; A61F 5/445; A61F 5/443; A61F 5/4404; A61F 5/4407
See application file for complete search history.

(56) References Cited

U.S. PATENT DOCUMENTS

| | | | |
|---|---|---|---|
| 2003/0220621 A1* | 11/2003 | Arkinstall | A61F 5/445 604/335 |
| 2010/0217213 A1 | 8/2010 | Forsell | |
| 2011/0015475 A1 | 1/2011 | Hanuka et al. | |
| 2011/0306823 A1* | 12/2011 | Gobel | A61F 5/445 600/32 |

(Continued)

FOREIGN PATENT DOCUMENTS

| | | |
|---|---|---|
| AU | 746371 | 8/1999 |
| AU | 2015230810 A1 | 10/2015 |
| BE | 899910 | 10/1984 |

(Continued)

OTHER PUBLICATIONS

International Search Report for PCT/IB2017/000045, dated May 16, 2017.

*Primary Examiner* — Kai H Weng
(74) *Attorney, Agent, or Firm* — Heslin Rothenberg Farley & Mesiti, P.C.

(57) ABSTRACT

The present invention relates to a biocompatible device that integrates electromagnetic and mechanical elements and allows the combination of different mechanisms for voluntary closing of the intestinal lumen. The device can be used either with a stoma to control intestinal transit to the outside and avoid the use of collection pouches, or without a stoma to regulate intestinal transit for another medically necessary reason.

11 Claims, 6 Drawing Sheets

(56) References Cited

U.S. PATENT DOCUMENTS

2013/0197458 A1\* 8/2013 Salama ................ A61F 5/4405
604/335
2015/0209173 A1\* 7/2015 Kratky .................... A61F 5/445
604/337

FOREIGN PATENT DOCUMENTS

CN 102834074 A 12/2012
ZA 8404164 A 2/1985

\* cited by examiner

SPHINCTER-TYPE INTESTINAL VALVE

CROSS REFERENCE TO RELATED APPLICATIONS

This application is a U.S. National Phase filing under 35 U.S.C. § 371 of International Application PCT/IB2017/000045, filed Jan. 27, 2017, and published as WO 2017/130055 A1 on Aug. 3, 2017. PCT/IB2017/000045 claims priority from Mexican Patent Application Number MX/a/2016/001395, filed Jan. 29, 2016 and Mexican Patent Application Number MX/a/2017/001193, filed Jan. 26, 2017. The entire contents of each of these applications are hereby incorporated herein by reference.

BACKGROUND

Currently, patients who suffer from any medical condition that affects intestinal integrity or proper transit of stool are candidates to undergo a surgical procedure which diverts intestinal transit outwards by exteriorizing an intestinal segment through the intestinal wall, thus avoiding the passage of bowel contents through the affected segment. This procedure is called "intestinal stoma" and can be performed either during emergency surgery or previously planned and scheduled.

There are several ways to classify intestinal stomata. One of them is by referring to the level at which the intestinal transit is exteriorized. Therefore, an intestinal stoma that exteriorizes the large intestine (colon) is called "colostomy", and one that exteriorizes the small intestine at any of its three sections—duodenum, jejunum and ileum—is called "duodenostomy", "jejunostomy" or "ileostomy", respectively. Under special circumstances, a stoma can be designed to divert the urinary tract in the same way as it diverts the stool, and this is called "ileal conduit".

The fecal or urinary output exiting through a stoma is generally contained in a pouch-type disposable reservoir, which is adhered around the exteriorized intestinal mucosa and is changed after use. However, given the high cost of the disposable collection pouch, as well as the harshness of the adhesive on the skin, the design of a device for voluntarily regulating the outward flow of stool was developed with the purpose of improving the quality of life of these patients and reducing the high costs associated with said condition since, in many cases, intestinal reconnection is not possible, creating an "irreversible stoma" status.

The main objective is to provide voluntary constraint of intestinal transit of a stoma via a sphincter-type intestinal valve, which is surgically implanted when creating the intestinal stoma by applying minimal changes to the standard technique described in the literature, or else implanted during a second surgical event in patients with an existing stoma. Said device can be mainly used in two different modes: as a stoma-regulating sphincter, which provides voluntary control for temporarily holding in the bowel contents, or as an electromagnetic valve in the absence of an intestinal stoma to contain intestinal transit to an intestinal segment specified by the surgeon to another damaged segment with specific therapeutic purposes and controlled by the patient using an external device.

The implementation of a device that allows voluntary regulation of fecal or urinary matter through an intestinal stoma would considerably increase the quality of life of these patients, since such a device has the ability to adapt cleaning accessories that ensure hygiene when draining the stool, in addition to having a cover or occluder that conceals the intestinal mucosa, removing the psychological impact associated with said condition.

The sphincter-type intestinal valve would significantly reduce the costs associated with this medical-surgical condition, not only for the patient but for the healthcare systems, improving the quality of life for millions of people. Furthermore, the electromagnetic intestinal valve would provide a valuable tool for treating various medical conditions in which intestinal transit is compromised.

Currently, no devices that have the described features and therapeutic purposes, integrating the mechanical and electromagnetic elements and supporting use in different modes, are found in the medical literature. Some relevant patents found are listed below, along with their most important differences with the sphincter-type intestinal valve.

Patent BE 899910 (1984)—A VALVE FOR CLOSING CUTANEOUS STOMA: This patent is a mechanical stomach valve, which is outside the patient's body, sealed by a cord and with suturing around the stoma.
   Differences: Since this invention relates to an external device for the stomach, it has a totally different system consisting of a cord, which does not include any electromechanical system or any elements similar to those included in this design, which, in principle, are intra-abdominal and pass through the abdominal wall to the outside of the body. The patent is a stomach valve and not an intestinal one;

Patent ZA8404164 (A) (1985)—VALVE FOR CLOSING A CUTANEOUS STOMA: This patent belongs to the same patent family as the preceding one, with the addition of pins that pass through the adipose tissue to connect the valve without further modification to the main mechanism.
   Differences: The addition of the pins for closure does not modify the main mechanism discussed, differing only in the stomach valve mechanism;

Patent CN102834074—MEDICAL DEVICE: This patent discloses a device that has an implant inside the patient's body, along with a discharge device, which is retained in the site of the stoma by magnetic means, and allows for hygienic discharge of intestinal waste.
   Differences: This device is designed for hygienic and practical disposal of the stool. Even though it has a similar mechanism of magnets and valves, its purpose, arrangement, installation and operating principles are completely different. It is an external device containing a tube that is inserted into the intestine, through which fecal matter exits towards a check valve. The device is attached externally to the patient's body, not sutured to the abdominal wall components, as is the case for the present device, and does not include an electromagnetic component or support use in different modes. Another relevant difference to note is the fact that it is not implanted surgically during stoma creation, and it cannot be adjusted or modified by the acting surgeon to suit the characteristics of each patient or stoma. Finally, it does not have any elements that allow it to be identified in X-rays by using barite material.

Patent AU746371—FOOD INTAKE RESTRICTION DEVICE: This patent relates to a device for restricting food through an elongate restriction device, which is used together with hydraulic operation means to restrict food intake.
   Differences: The system and the purpose are completely different from the disclosure of this invention, since the scope of this design does not mention food intake restriction or the use of a hydraulic system.

BRIEF DESCRIPTION OF THE INVENTION

The present invention refers to a sphincter-type intestinal valve for voluntarily regulating intestinal transit, with or without intestinal stomata, which comprises a biocompatible tubular intestinal casing having an adjustable biocompatible electromagnetic valve arranged in said casing; a mechanical intestinal valve arranged at a free end of said biocompatible tubular intestinal casing; a check valve arranged at a free end of said mechanical intestinal valve, which is coupled with the free end of the mechanical intestinal valve, and where the free end of the check valve is in contact with the outside; and a sealed rotary occluder that seals the free end of the check valve.

BRIEF DESCRIPTION OF THE FIGURES

The illustrative embodiment can be described in reference to the accompanying figures, which relate to.

DETAILED DESCRIPTION

The following description refers to FIGS. 1 to 6 interchangeably.

Figure 1:
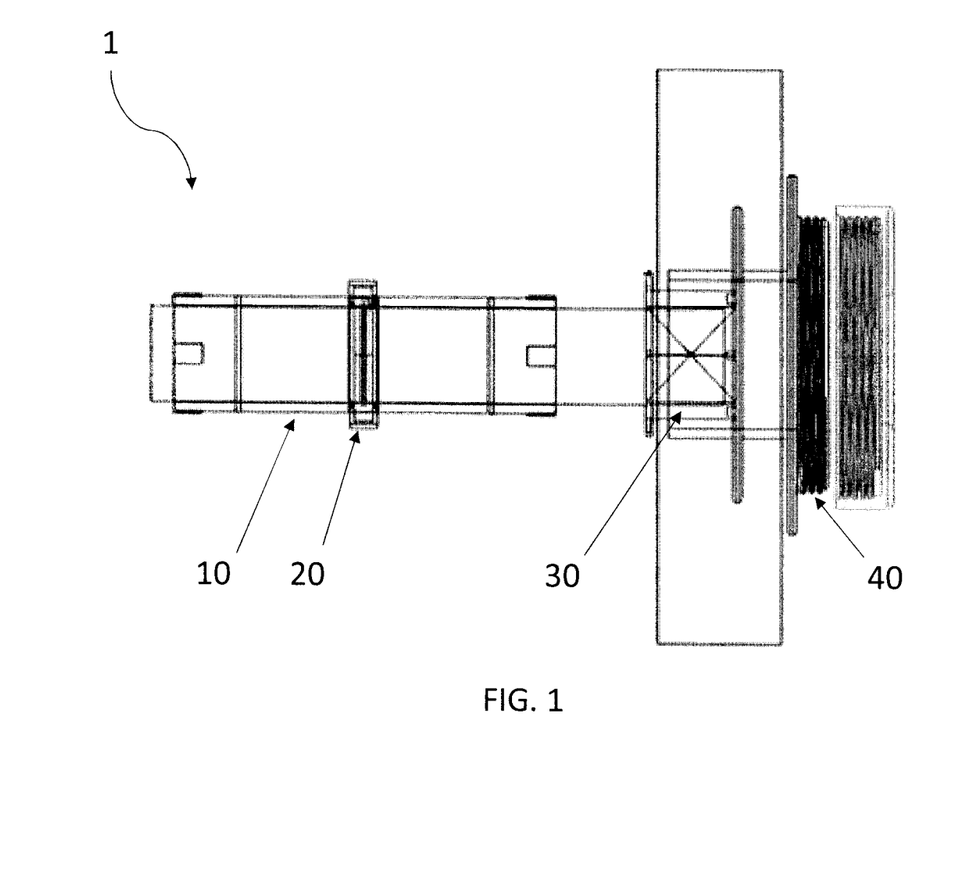
FIG. 1 is a side view of the assembly of the sphincter-type intestinal valve in an intestinal segment in its final position.

The sphincter-type intestinal valve (1) referred to in this invention allows for voluntary regulation of intestinal transit in any segment of the small intestine or colon according to the specific needs of the surgeon or patient, either with or without an intestinal stoma, which can be used in two different embodiments: first, as an artificial sphincter of an intestinal stoma, and second, as an electromagnetic intestinal containment valve in the absence of a stoma.

Said different embodiments are achieved by a design that allows the implantation of two main elements: an adjustable biocompatible electromagnetic valve and a sphincter-type biocompatible mechanical intestinal valve. The elements that make up the abovementioned structures are shown clearly in the following description and accompanying drawings.

Figure 2:
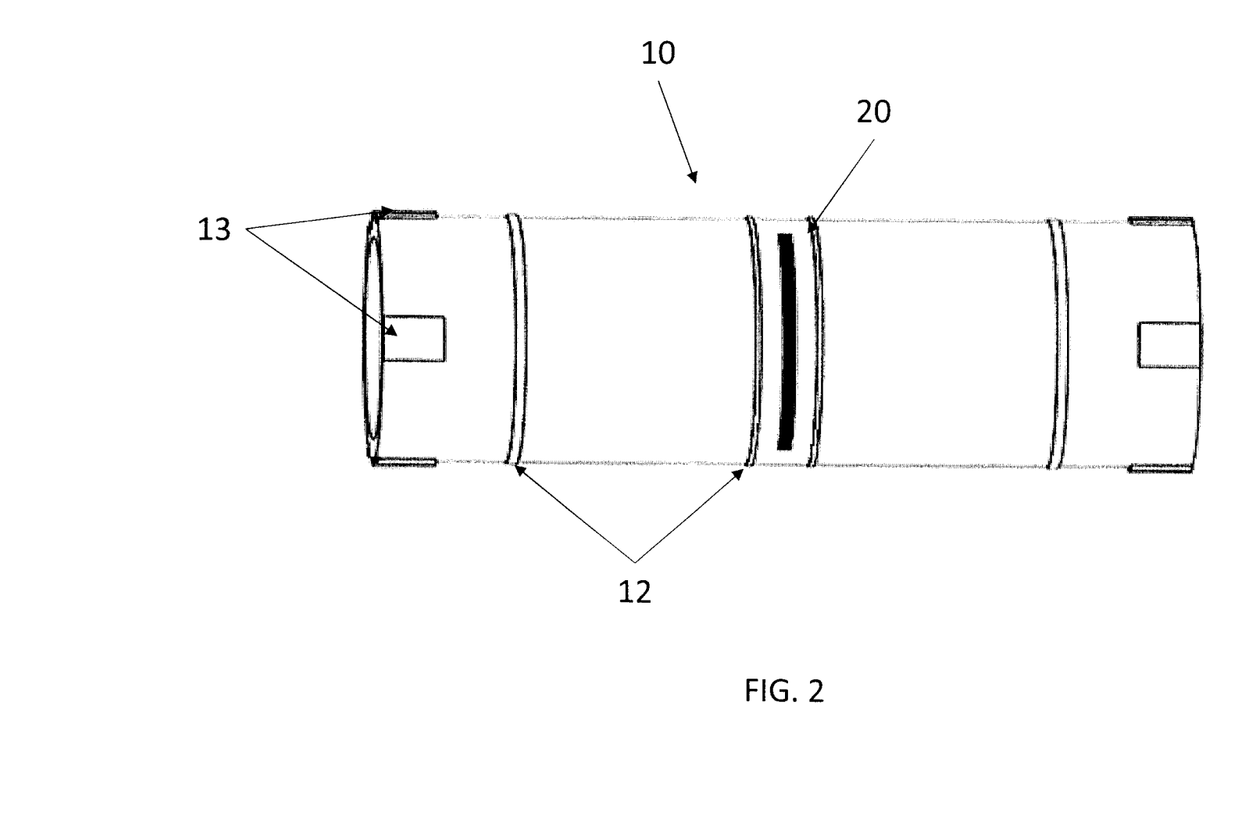
FIG. 2 is a side view of the biocompatible tubular intestinal casing.

The biocompatible tubular intestinal casing (10) comprises a thin film made of a biocompatible material, which can cover a specific intestinal segment of various lengths, and allows the adjustable biocompatible electromagnetic valve (20) to be attached to its structure and to the intestinal wall, while also protecting the intestinal segment used. Said structure consists of a barium thread (12) arranged circumferentially at the ends and halfway along the length thereof, allowing said structure to be identified along the entire length thereof, as well as biocompatible support bearings (13) arranged cardinally around the edges of the ends allowing attachment either to the intestinal serosa or to other anatomical or valvular structures, accordingly.

Figure 3:
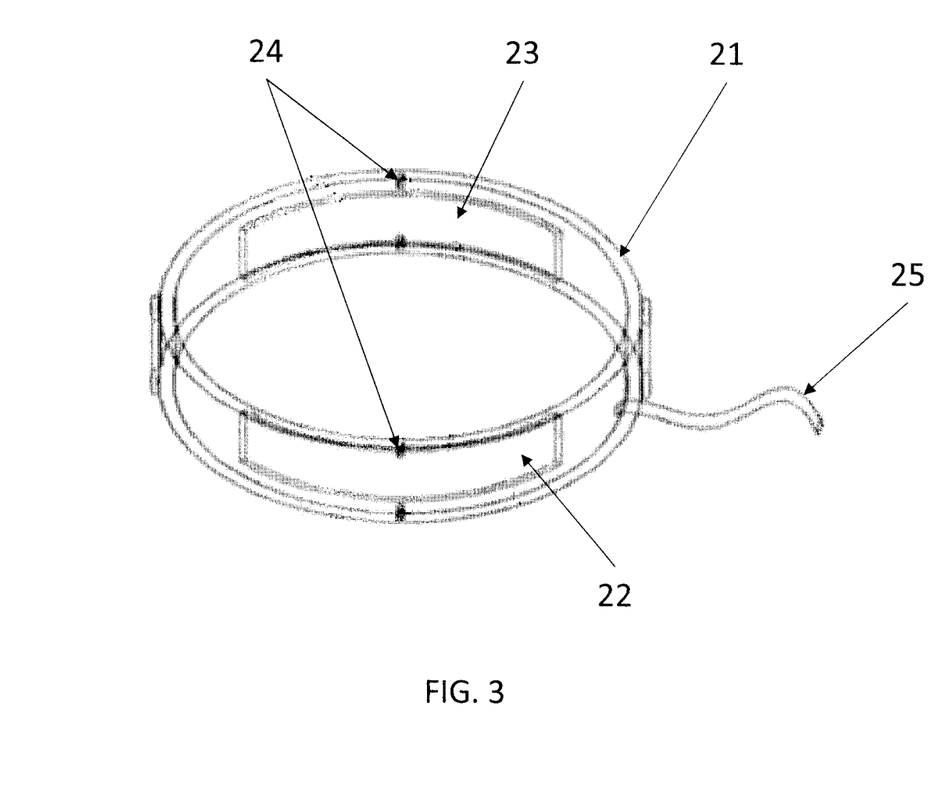
FIG. 3 is a perspective view of the adjustable biocompatible electromagnetic valve.

The biocompatible adjustable electromagnetic valve (20) is mainly made up of a biocompatible support structure (21) which can be attached directly either to the intestine or to the biocompatible tubular intestinal casing (10). Two electromagnets are provided inside the biocompatible support structure: one with positive polarity (22) and the other with negative polarity (23), arranged one in front of the other and providing direct compression when activated, thus collapsing the intestinal lumen of the segment being used. The valve is secured in any position by the holes (24) that allow the surgeon to suture it at the appropriate point. The electromagnets have an individual internal cable that connects to the cable of the opposite-pole magnet through the inside of the biocompatible support structure, and together they constitute the biocompatible support cable (25) which connects both polarities. The biocompatible cable is exteriorized during the surgical procedure by a counter-opening through the abdominal wall to connect to the rechargeable external device (50), which supplies electrical power to activate the electromagnets.

Figure 6:
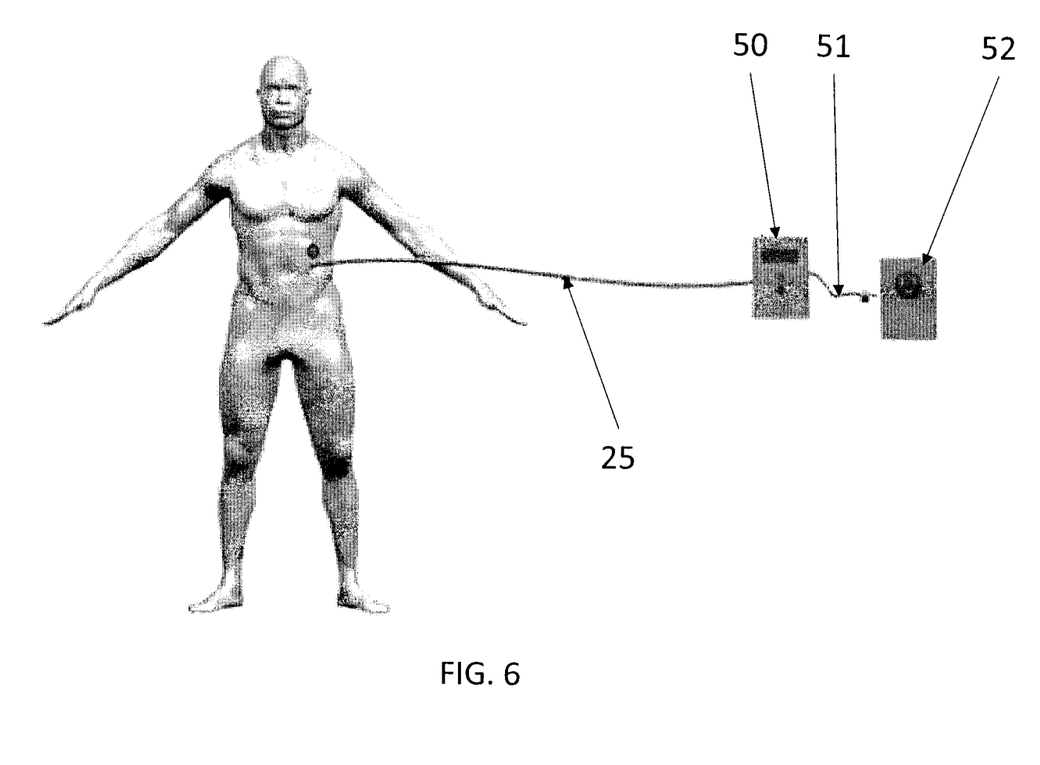
FIG. 6 is an external, panoramic view of the rechargeable external device.

The rechargeable external device (50) is a device that generates an electrical signal that activates the magnets (22, 23), which in turn allow intestinal closure by attracting one another. Said activation signal is transmitted either through the biocompatible cable (25) or wirelessly, generating the activation signal within a distance range close to the patient. The device may be rechargeable by a conventional external power cable (51) plugged into an electrical outlet (52) or by using batteries.

Figure 4:
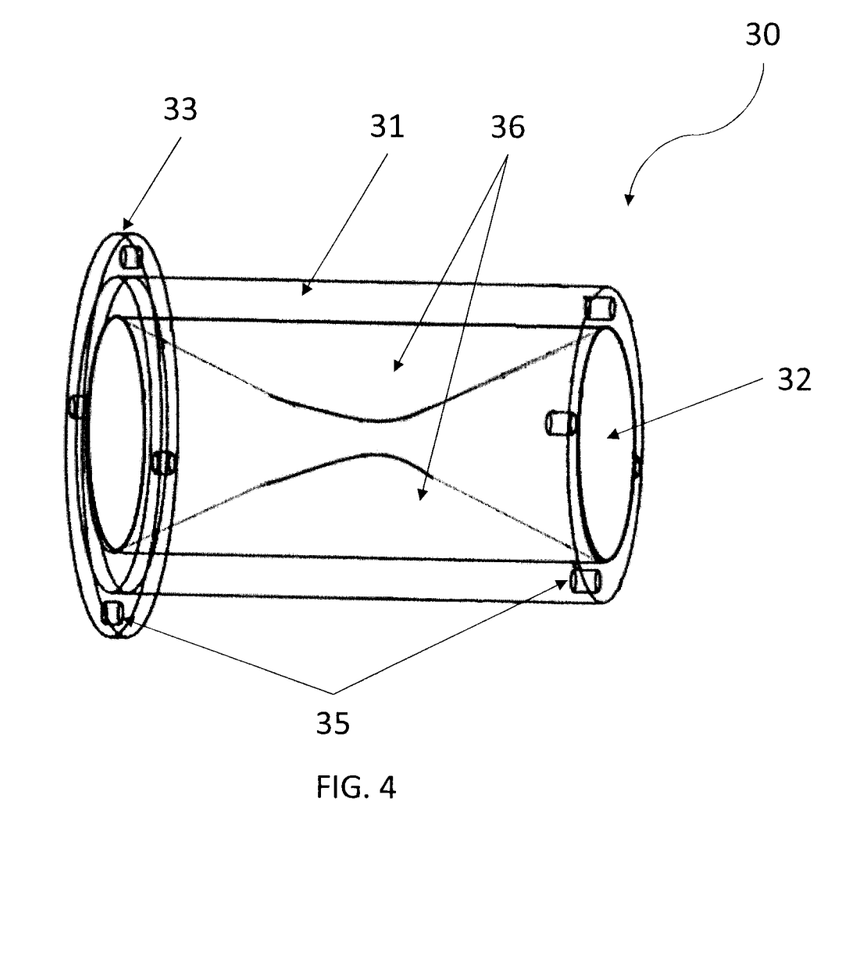
FIG. 4 is a perspective view of the mechanical valve.

The mechanical intestinal valve (30) is selected from the group of on/off valves, so that the mechanical valve has only two positions: a first position allowing the passage of fluid therethrough, and a second position preventing the passage of fluid therethrough.

In one embodiment, the mechanical intestinal valve (30) is made up of a rigid cylindrical structure (31) made of a biocompatible material, which allows the mechanical sealing of the intestinal lumen (32). This valve is able to extend its length in accordance with the overall thickness of the abdominal wall (100) by integrating the biocompatible intestinal structure (10). The attachment of the elements that make up the valve to the entire abdominal wall from the innermost layer (peritoneum) to the outermost layer (skin) is carried out via two main mechanisms: first, by the inflammatory reaction which generates scar tissue (fibrosis) and seals the spaces between the devices and the abdominal wall; second, through the biocompatible bearings (13) and the holes (35) in the inner (33) and outer clamps (not shown), stabilizing the device on the structures as required through the use of absorbable suture material.

The mechanical intestinal valve (30) is also activated via two mechanisms activated manually by either the patient or another person. The first mechanism activates two lateral symmetrical resistances (36) which collapse the intestinal lumen due to the extrinsic compression of the intestine, thus closing the intestinal lumen (32).

Figure 5:
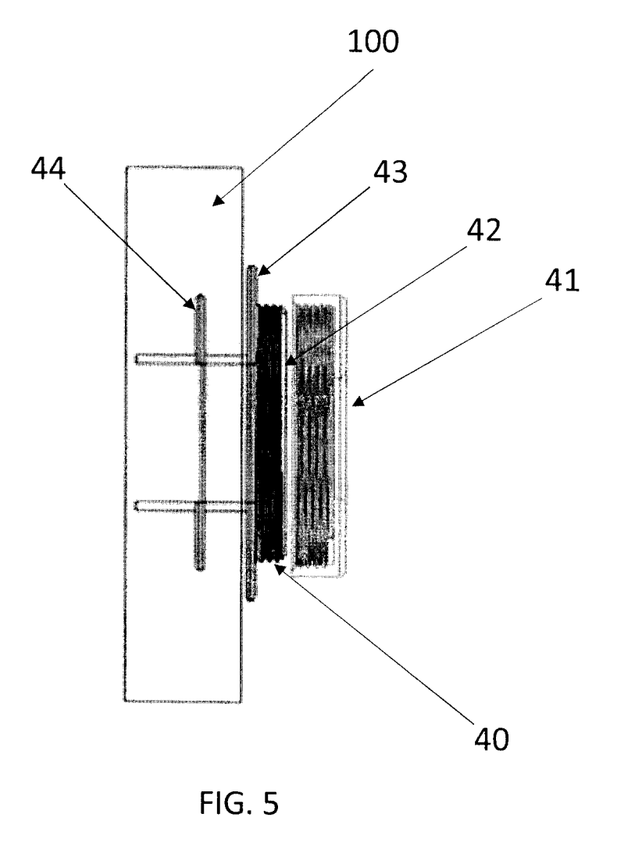
FIG. 5 is a view of the check valve and the sealing occluder.

The second closing mechanism is performed by a check valve (40). When a sealing occluder (41) closes, it pushes a circumferential metal resistance (42) that prevents the gradual passage of stool. The check valve (40) is deactivated, allowing the decompression of the circumferential metal resistor (42), which then returns to its initial position, allowing the flow. Said valve (40) has circular clamps (43, 44) on its outer and inner edges, which allow the device to be attached to an anatomical structure or to parts of the device. In the specific case of the inner clamp (44), it allows attachment either to the abdominal wall components (100)

or to the biocompatible tubular structure (10), so as to achieve the extension required for very obese patients. In the specific case of the outer clamp (43), it is in contact with the skin, allowing cutaneous attachment, as well as the adaptation of accessories for draining or cleaning the stoma and the sealed rotary occluder (41).

A person skilled in the art may modify the structure described herein. However, it should be noted that this description relates to preferred embodiments of the invention, and is provided for illustrative purposes only, and should not be understood as limiting the invention. All obvious modifications in the spirit of the invention, such as changes in the shape, material and dimensions of the elements that make up the invention, should be considered within the scope of the appended claims.

The invention claimed is:

1. A sphincter-type intestinal valve for regulating intestinal transit, comprising:
   a biocompatible tubular intestinal casing having an adjustable electromagnetic valve arranged on said casing;
   a mechanical intestinal valve arranged at a free end of said biocompatible tubular intestinal casing;
   a check valve arranged at a free end of said mechanical intestinal valve, which is coupled with a free end of the intestinal mechanical valve, and in which a free end of the check valve is configured to be in contact with the outside; and
   a sealed rotary occluder which seals the free end of the check valve.

2. The sphincter-type intestinal valve as referred to in claim 1, wherein the intestinal valve adapts to the thickness of an intestinal wall of a patient by integrating the biocompatible tubular intestinal casing, so that the biocompatible tubular intestinal casing is extended and subsequently cut as required.

3. The sphincter-type intestinal valve as referred to in claim 1, wherein the mechanical intestinal valve is activated through a rotation of the sealed rotary occluder, activating two resistances is configured to occlude an intestinal lumen and configured to compress side walls of an intestine.

4. The sphincter-type intestinal valve as referred to in claim 1, wherein either the check valve or the sealed rotary occluder using a check valve mechanism regulate the gradual passage of intestinal residue.

5. The sphincter-type intestinal valve as referred to in claim 1, wherein the the adjustable electromagnetic valve is made up of a cylindrical support structure that holds two electromagnets with opposite poles which, when activated by an electric current, generate a occlusion of an intestinal lumen.

6. The sphincter-type intestinal valve as referred to in claim 1, wherein the biocompatible tubular intestinal casing is a tubular structure made of a biocompatible material and having a variable length, wherein the variable length of said tubular structure allows attachment to a specific intestinal segment or to other anatomical or valvular structures as required.

7. The sphincter-type intestinal valve as referred to in claim 6, wherein said tubular structure is identified in X-rays due to a circumferential and symmetrical arrangement of radiopaque barium thread at either end and at the middle of the tubular structure for identification purposes.

8. The sphincter-type intestinal valve as referred to in claim 5, wherein an external device supplies power to the electromagnets, and interrupts or establishes a flow of electricity.

9. The sphincter-type intestinal valve as referred to in claim 5, wherein the electromagnets are attached to the cylindrical support structure by a binding band, and in which a cable that powers the electromagnets comes out through the binding band and is exteriorized via a hole near a stoma in order to connect to a rechargeable external device.

10. The sphincter-type intestinal valve as referred to in claim 1, wherein the intestinal valve is configured to be placed in and attached at any level of an intestine, with or without the presence of an intestinal stoma, by means of an absorbable suture material.

11. The sphincter-type intestinal valve as referred to in claim 1, which is activated wirelessly or by manually activating a rechargeable external device.

* * * * *